(12) United States Patent
Hikichi

(10) Patent No.: US 6,902,585 B2
(45) Date of Patent: Jun. 7, 2005

(54) ABOVE-KNEE PROSTHESIS WITH VARIABLE RESISTANCE KNEE JOINT

(76) Inventor: Yuichi Hikichi, 1-14-19 Hinokicho, Yamagata-shi, Yamagata (JP) 990-0813

( * ) Notice: Subject to any disclaimer, the term of this patent is extended or adjusted under 35 U.S.C. 154(b) by 4 days.

(21) Appl. No.: 10/707,732

(22) Filed: Jan. 7, 2004

(65) Prior Publication Data

US 2005/0015156 A1    Jan. 20, 2005

(30) Foreign Application Priority Data

Jul. 17, 2003    (JP) ............................ 2003-275716

(51) Int. Cl.[7] ............................................. A61F 2/64
(52) U.S. Cl. ...................................................... 623/45
(58) Field of Search .................... 623/39–45

(56) References Cited

U.S. PATENT DOCUMENTS

| | | | |
|---|---|---|---|
| 5,007,933 A | 4/1991 | Sidebotham et al. | ......... 623/20 |
| 5,133,773 A | 7/1992 | Sawamura et al. | ............ 623/24 |
| 5,593,449 A | 1/1997 | Robertson, Jr. | .......... 623/20.36 |
| 5,904,721 A * | 5/1999 | Henry et al. | ................... 623/26 |
| 6,113,642 A * | 9/2000 | Petrofsky et al. | ............. 623/24 |

FOREIGN PATENT DOCUMENTS

| | | |
|---|---|---|
| JP | (Showa)52-47638 | 9/1973 |
| JP | (Heisei)11-19105 | 1/1999 |

\* cited by examiner

Primary Examiner—Bruce E Snow
(74) Attorney, Agent, or Firm—Seth M. Reiss

(57) ABSTRACT

An above-knee prosthesis that allows the user to control the resistance of knee flexion or extension, and to voluntary lock and release the knee joint, at any and all bending angles, comprising a thigh frame assembly that receives a thigh stump; a leg frame assembly with foot attached; a hinge interconnecting the thigh frame and leg frame assemblies to form an artificial knee joint; a closed hydraulic system further interconnecting the thigh frame and leg frame assemblies to provide resistance to the bending of said artificial knee joint, a means to vary the resistance provided by said closed hydraulic system, and a means to translate the AP movement of said thigh stump into the degree of resistance provided by said closed hydraulic system. In its preferred embodiments, the AP movement of the thigh stump is communicated by means of a linkage, sliding or screw assembly, to a flow rate control valve. The flow rate control valve varies the amount of the resistance provided by the closed hydraulic system controlling, thereby, the amount of resistance within the artificial knee. Pressing the thigh stump backwards within the thigh frame assembly increases the resistance within the hydraulic system and slows knee bending until the knee locks. Pressing the thigh stump forward decreases the hydraulic resistive force and allows the artificial knee joint to yield to outside forces, such as gravity and/or stump thrust, until the prosthesis rotates freely about the knee hinge. The above-knee prosthetic prevents the knee joint from giving way, promotes a balanced stance, and facilitates a near normal reciprocating gate while ascending and descending stairs and slopes.

20 Claims, 10 Drawing Sheets

ABOVE-KNEE PROSTHESIS WITH VARIABLE RESISTANCE KNEE JOINT

CROSS-REFERENCE TO RELATED PATENT APPLICATIONS

This application claims the benefit of Japanese Patent Application No. 2003-275716 filed Jul. 17, 2003, by the same inventor.

STATEMENT REGARDING FEDERALLY SPONSORED RESEARCH OR DEVELOPMENT

The subject invention is not the result of or in any way related to a federally sponsored research or development.

TECHNICAL FIELD

The invention relates to a knee joint for an above-knee prosthesis. More particularly, this invention describes a hydraulically controlled knee-joint for an above-knee prosthesis that allows the user to control the resistance of knee flexion and extension at all bending angles.

BACKGROUND ART

Artificial legs having knee joints, commonly referred to as above-knee prosthesis, are well known and understood. A variety of such prosthetic devices have been described in the available literature and many styles and types are commercially available.

Preventing the giving way of the knee when in stance phase is of critical importance for trans-femoral prosthetic device users in order to prevent the user from falling down. In this regard, various kinds of artificial knee joints that perform stance phase control, including load brake knee, have been put into practice to prevent the giving way of the knee. However, none of the known devices that have been used to prevent the giving way of artificial knee joints are capable of controlling knee movement at any bending angle. An object of the present invention is to provide a trans-femoral prosthetic device that allows the user to prevent the artificial knee from giving way at any and all bending angles.

Another limitation of known above-knee prostheses is their inability to allow the user to ascend and descend stairs and slopes using a reciprocating gait. Some known prosthetic devices incorporate a mechanism that facilitates a reciprocating gait while descending stairs and slopes. When the user rests his or her weight on the prosthesis while bending (flexing or extending) the artificial knee, the resistance of knee bending is increased causing the bending to slow. While suitable for descending stairs and slopes, these devices cannot enable a reciprocating gait when ascending stairs or slopes. It is a further object of the present invention to provide an above-knee prosthesis that facilitates a reciprocating gait close to normal while both ascending, and descending, stairs and slopes.

Also known are trans-femoral prostheses having knee joints that employ sensors able to detect muscle contractions of the thigh stump in conjunction with hydraulic or pneumatic systems to control knee joint resistance. Such devices require a specialized socket to receive the thigh stump, adding to the system's complexity and overall cost. A further object of the present invention is to provide an above-knee prosthesis that functions to control knee joint resistance at all knee joint angles, without the use of electronic controls, that is simple in design, and can be produced and employed at modest expense.

DISCLOSURE

These and other problems are solved by the subject invention, an above-knee prosthesis comprising an artificial knee joint, a closed hydraulic system that interconnects with the prosthesis above and below the knee joint to control the resistance of the knee flexion and extension at any bending angle, means to vary the amount of resistance provided by the hydraulic system to the artificial knee joint, and a means to communicate the anterior-posterior (AP) movement of the user's thigh stump to the hydraulic system to vary the resistance of knee bending.

The user of this novel above-knee prosthesis can decrease the resistance of flexion or extension of the artificial knee joint by moving his or her thigh stump in an anterior direction until the knee joint rotates freely. Conversely, the user can increase the resistance of bending the knee joint, whether during flexion or extension, by moving the thigh stump in a posterior direction until the knee joint, ultimately, locks. The user is thus able to control the resistance in the artificial knee joint mechanically, without the use of electronic sensors, and without being fitted with a specialized socket that receives the thigh stump.

The anterior-posterior (AP) movement of the thigh stump is communicated to a hydraulic valve that controls the rate of flow of hydraulic fluid to and away from a hydraulic cylinder with piston. The cylinder with piston affects the rate at which the knee joint flexes and extends when a given force is applied. The ability to increase or decrease the resistance of the bending of the knee joint is unaffected by the angle of the knee joint, and thus available to the user at any bending angle. By increasing the resistance of the knee joint until the knee joint locks, the above-knee prosthesis is prevented from giving way.

A knee joint of an subject invention provides the user with confidence against the knee joint giving way, or drop-off, during normal walking operations since the user has the ability to increase knee resistance, and lock the knee joint, at any time during the walking cycle, regardless of the point in the cycle or the angle at which the knee joint is bent. Using the hip joint extensor muscles of an amputated thigh stump, the wearer can ascend and descend slopes and stairs demonstrating a reciprocating gait. By selective contraction of the hip joint extensor and hip joint flexor muscles of the amputated thigh stump, the wearer controls knee lock, knee yielding, and free knee swing motions voluntarily.

Given the invention's simple structure and non-reliance on electronic controls, sensors and specialized sockets, the above-knee prosthesis of the subject invention can be manufactured and provided to consumers at a relative low cost.

DETAILED DESCRIPTION OF PREFERRED EMBODIMENTS

Figure 1:
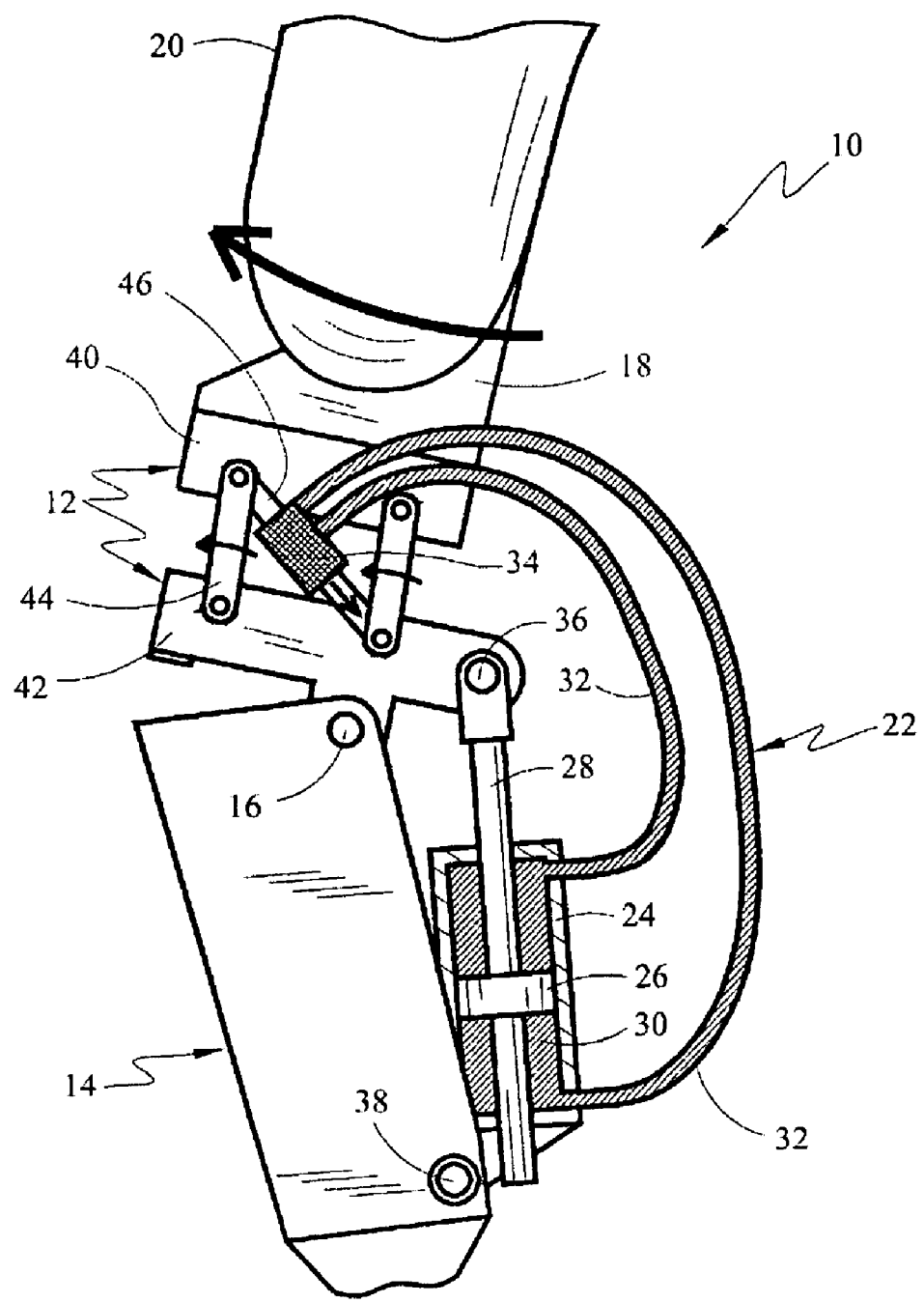
FIG. 1 is a left side view of a first preferred embodiment of the above-knee prosthesis of the present invention, the right side view being a mirror image thereof, showing the thigh stump being moved in an anterior direction to decrease the resistance of bending the artificial knee joint.
Figure 2:
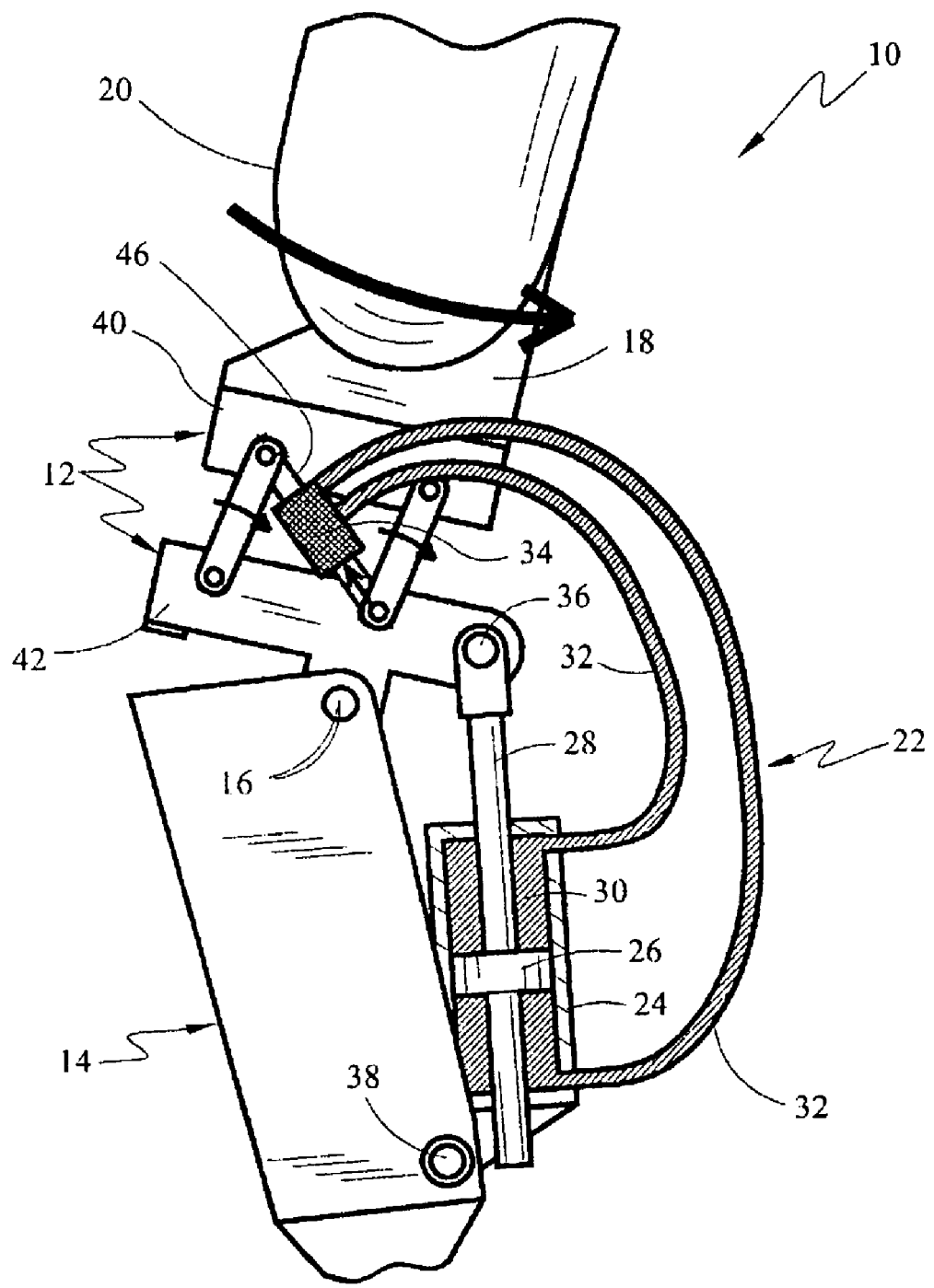
FIG. 2 is a left side view of the above-knee prosthesis of FIG. 1 showing the thigh stump being moved in a posterior direction to increase the resistance of bending the artificial knee joint.

Illustrated in FIGS. 1 and 2 is a first preferred embodiment 10 of the above-knee prosthesis of the present invention, comprising a thigh frame assembly 12 that is rotatably connected to a leg frame assembly 14 by a knee pin 16, forming thereby, an artificial knee joint. A socket 18 is secured to the upper aspect of thigh frame assembly 12. Socket 18 may be hollow, with its upper aspect open to receive a femoral stump 20.

The degree of resistance of rotation of thigh frame assembly 12 relative to leg frame assembly 14 about knee pin 16 is controlled by a closed hydraulic system 22. Hydraulic system 22 comprises a hydraulic cylinder 24 housing a piston 26 attached to a piston rod 28 surrounded by a hydraulic fluid 30. System 22 further comprises tubing 32 that communicates the hydraulic fluid 30 between cylinder 24 and a hydraulic flow rate control value 34.

Closed hydraulic system 22 controls the resistance of bending of artificial knee 16 by interconnecting thigh assembly 12 and leg assembly 14. System 22 is rotatably fixed to thigh assembly 12 through the upper aspect of piston rod 28 and a piston rod pin 36. System 22 is rotatably fixed to leg assembly 14 through the lower aspect of cylinder 24 and a cylinder housing pin 38.

According to the first preferred embodiment depicted in FIGS. 1 and 2, thigh frame assembly 12 is further comprised of an upper frame block 40 and a lower frame block 42. Upper frame block 40 and lower frame block 42 are interconnected, one to the other, through a linkage mechanism 44 having four links (the two right side links being identical to the two left side links shown). Linkage mechanism 44 communicates the AP movement of upper block 40 relative to lower block 42 to control hydraulic valve 34 by displacement of a linkage rod 46.

The manner of operation of the first preferred embodiment 10 of the above-knee prosthesis of the subject invention is illustrated first with reference to FIG. 1. Thigh stump 20 is moved by the user in an anterior direction by contraction of the hip joint flexor muscles in the amputated thigh stump. The anterior movement of socket 18 moves upper block 40 in an anterior direction relative to lower block 42, causing linkage mechanism 44 to displace linkage rod 46 and open flow rate control valve 34. Once opened, valve 34 allows hydraulic fluid 30 to move more freely within tubing 32. This, in turn, allows hydraulic piston 26 to move more freely within hydraulic cylinder 24, permitting thigh frame assembly 12 to rotate more freely about knee pin 16, and to move more freely relative to leg frame 14. As thigh stump 20 continues to move in an anterior direction, valve 34 opens fully, the flow of hydraulic fluid 32 is uninhibited, and thigh and leg assemblies 12 and 14 can rotate freely around knee pin 16 without resistance.

FIG. 2 illustrates the use of above-knee prosthesis 10 to increase the resistance of the artificial knee joint to the point where the artificial knee joint locks. As shown in FIG. 2, thigh stump 20 is moved by the user in a posterior direction through contraction of the hip joint extensor muscles. The posterior movement of socket 18 moves upper block 40 in a posterior direction relative to lower block 42, causing linkage mechanism 44 to close hydraulic control valve 34 through displacement of rod 46. As it is closed, valve 34 impedes the flow of hydraulic fluid 30 within tubing 32. This, in turn, inhibits the movement of piston 26 within hydraulic cylinder 24, causing thigh assembly 12 to resist being rotated about knee pin 16 and to instead maintain its angle relative to leg frame 14. As thigh stump 20 continues to move in a posterior direction, valve 34 closely fully, halting the flow of hydraulic fluid 30, causing piston 26 is seize within cylinder 24, freezing the angle between thigh frame assembly 12 and leg frame assembly 14, and causing the artificial knee to lock.

Figure 3:
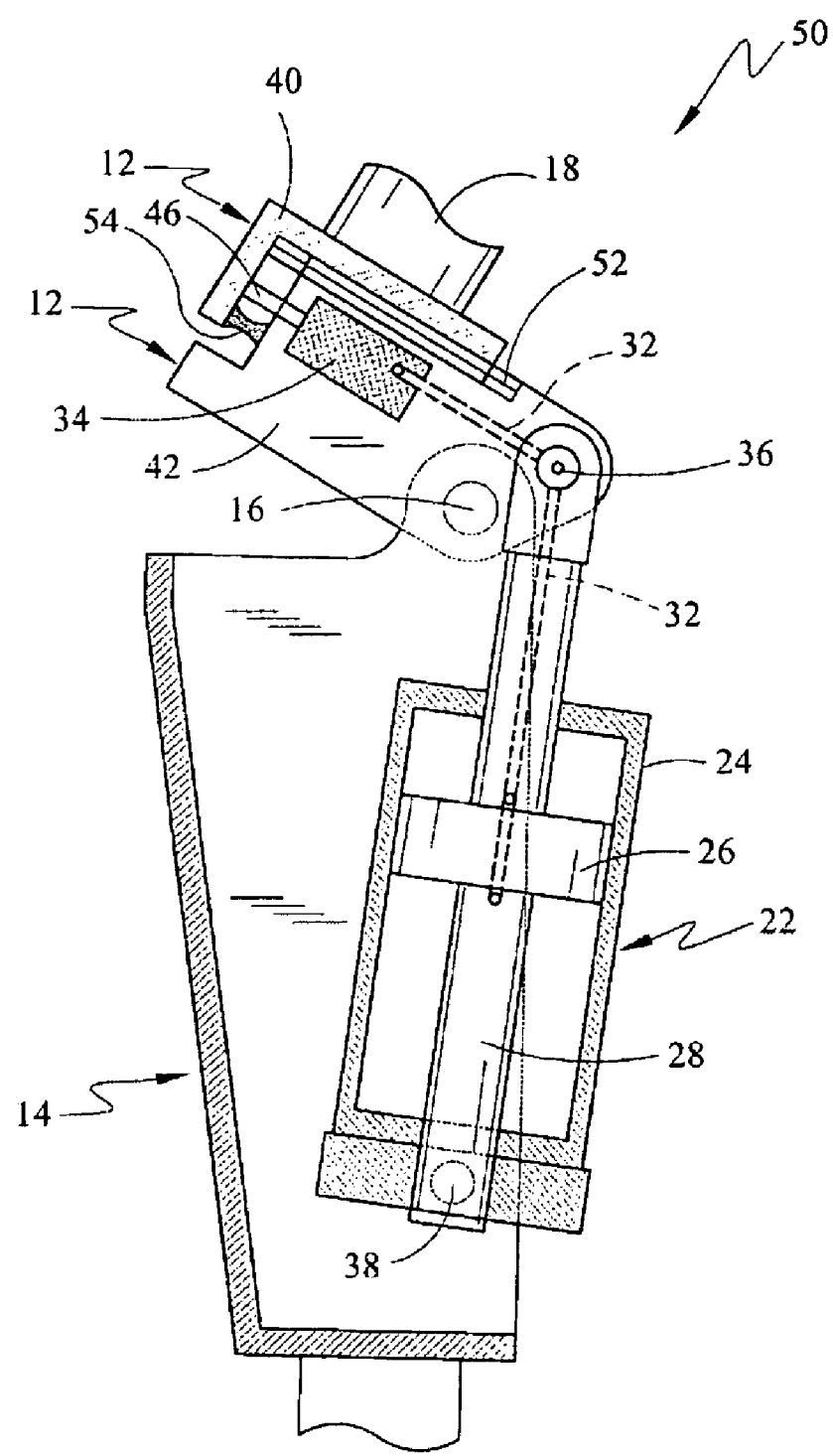
FIG. 3 is a left side view of a second preferred embodiment of the above-knee prosthesis of the present invention, the right side view being a mirror image thereof, showing the thigh stump being moved in an anterior direction to decrease the resistance of bending the artificial knee joint.
Figure 4:
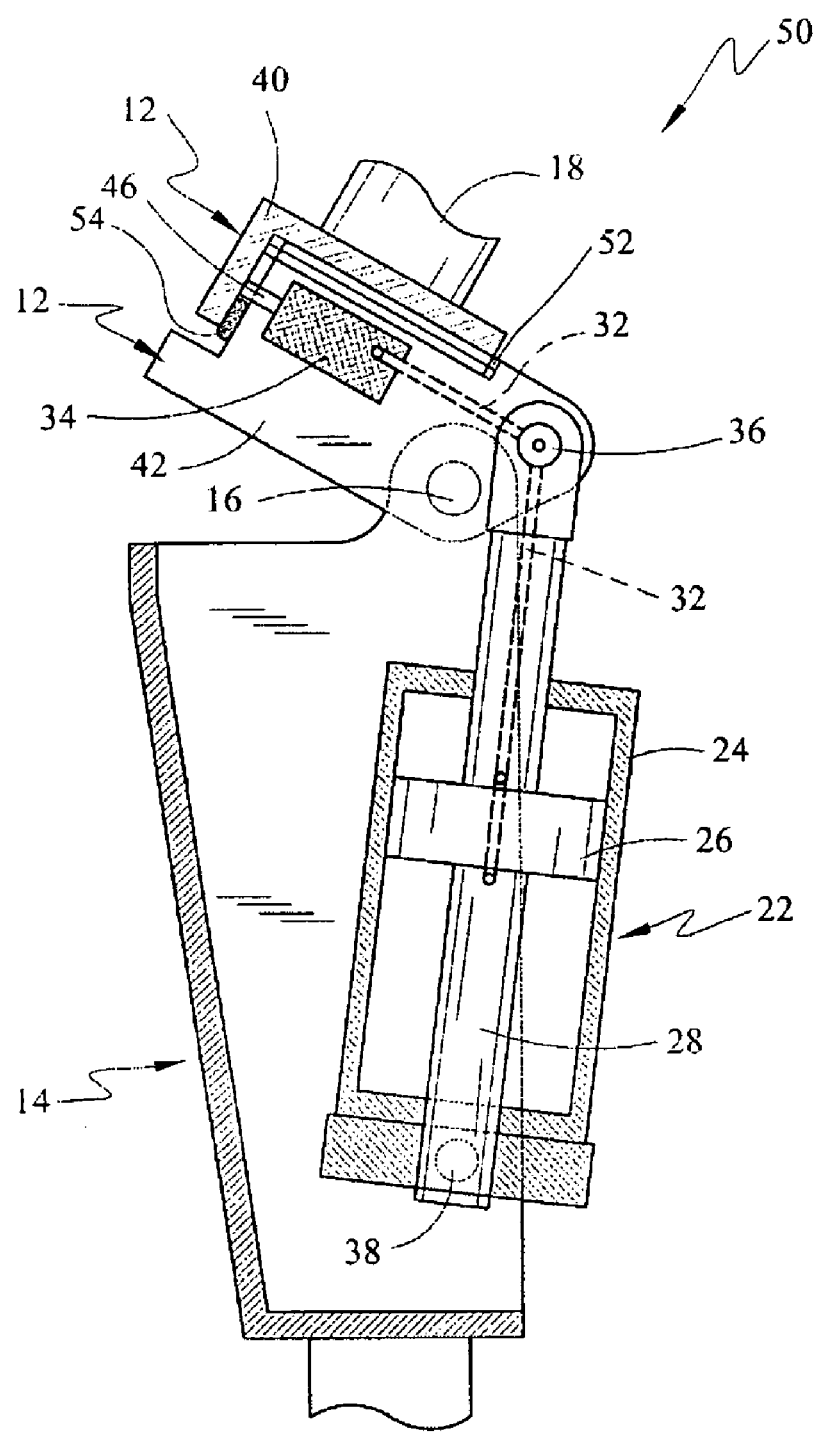
FIG. 4 is a left side view of the above-knee prosthesis of FIG. 3 showing the thigh stump being moved in a posterior direction to increase the resistance of bending the artificial knee joint.

FIGS. 3 and 4 depict a second preferred embodiment 50 of the above above-knee prosthesis of the present invention. Prosthesis 50 employs a different means for communicating the AP movement of the thigh stump to closed hydraulic system 22 and houses hydraulic system 22 partially within leg frame assembly 14.

Although partially hidden within leg assembly 14, hydraulic system 22 interconnects thigh assembly 12 and leg assembly 14 to provide resistance to knee bending in the same manner as hydraulic system 22 in above-knee prosthesis 10. The upper aspect of system 22 is rotatably fixed inside thigh assembly 12 through piston rod 28 and piston rod pin 36, and the lower aspect of hydraulic system 22 is rotatably fixed within leg frame assembly 14 through cylinder housing pin 38.

According to this embodiment, thigh frame assembly 12 is comprised of upper frame block 40, lower frame block 42, and a slide rail 52 that permits upper block 40 to slide relative to lower block 42. A damper 54 is fitted under a lip of upper block 40 to dampen the abutment of blocks 40 and 42 during the slide phase. As in the earlier embodiment, socket 18 that receives thigh stump 20 (not shown in FIGS. 3 and 4) is attached to the upper surface of upper block 40.

As upper block 40 slides relative to lower block 42, linkage rod 46 is displaced causing the opening and closing of flow rate control valve 34. Hydraulic fluid 30 flows from control valve 34 through hydraulic tubing 32 housed, according to this second preferred embodiment, within thigh frame assembly 12 and hydraulic system 22.

In FIG. 3, the user has flexed his or her thigh stump to release the resistance in the artificial knee. Upper block 40 has been slid in an anterior direction relative to lower block 42 and leg frame 12, causing linkage rod 46 to be displaced and open valve 34. Hydraulic fluid flows freely within tubing 32 while piston 26 moves freely within cylinder 24, allowing the artificial knee to bend without resistance.

In FIG. 4, the user has extended his or her thigh stump to increase the resistance of bending the artificial knee or to lock the artificial knee. Upper block 40 has been slid in a posterior direction relative to lower block 42 and leg assembly 12, causing linkage rod 46 to close valve 34. Hydraulic fluid is inhibited from flowing freely within tubing 32 and piston 26 resists movement within cylinder 24, causing the artificial knee to seize up and lock.

Figure 5:
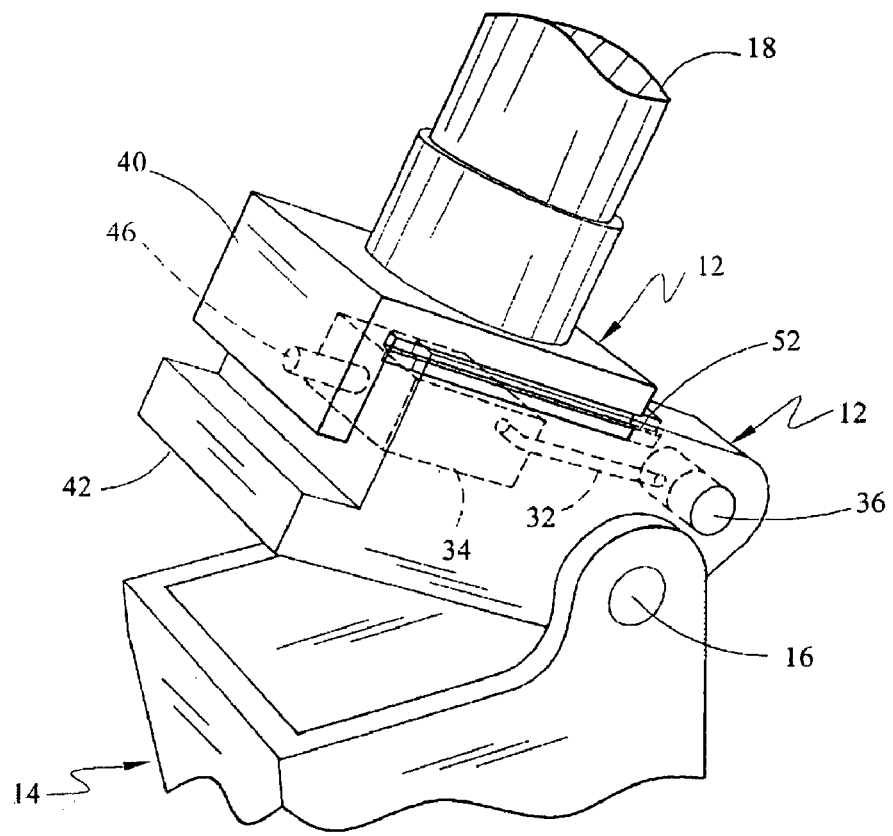
FIG. 5 is a left side perspective view of the thigh frame assembly of the above-knee prosthesis of FIG. 3 showing the flow rate control valve housed within the thigh assembly.

Details of the thigh frame assembly 12 of the second preferred embodiment above-knee prosthesis 50 are illustrated in FIG. 5. Thigh frame assembly 12 of prosthesis 50 houses flow rate control valve 34. Socket 18 is attached to upper block 40. Slide rail 52 is sandwiched between upper block 40 and lower block 42. As upper block 40 slides relative to lower block 42, linkage rod 46 is displaced and either opens, or closes, flow rate control valve 34. Hydraulic tubing 32 shown extending from control valve 34 communicates the rate of flow of fluid 30 to hydraulic cylinder 24 (shown in FIGS. 3 and 4).

Figure 6:
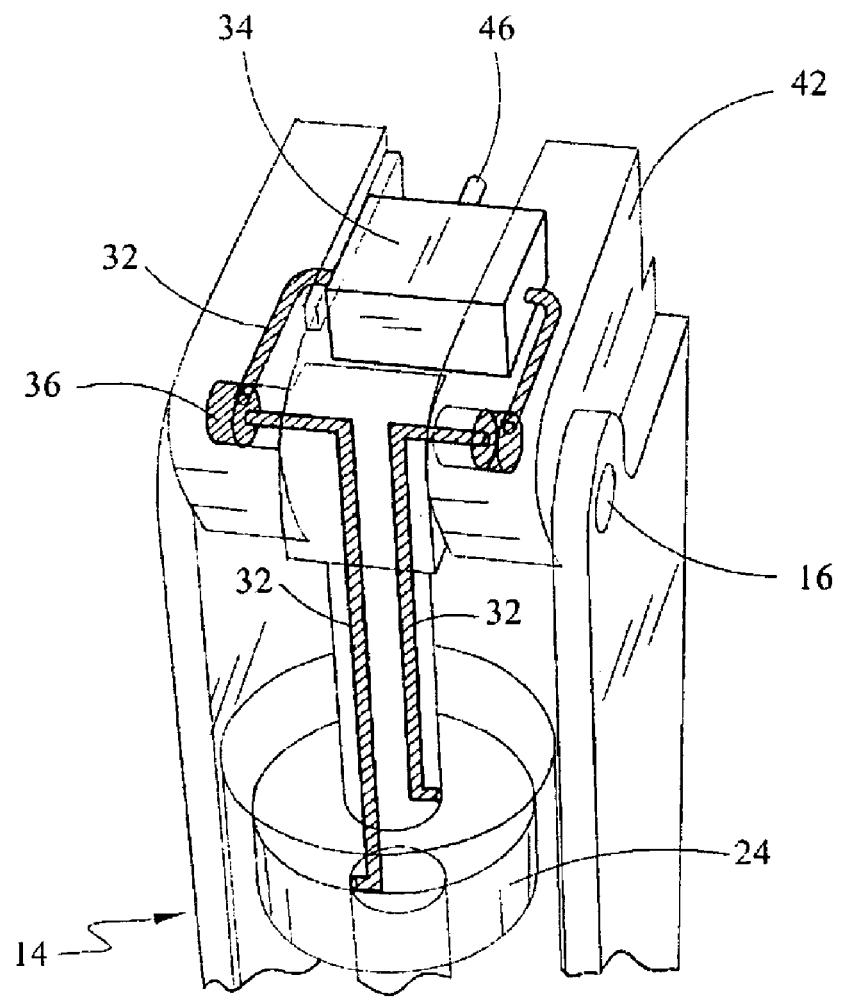
FIG. 6 is a top perspective view of the thigh frame assembly of the above-knee prosthesis of FIG. 3 showing the hydraulic tubing enclosed within the thigh assembly and hydraulic system components.

One manner of enclosing hydraulic tubing 32 within thigh assembly 12 and hydraulic system 22 is depicted in FIG. 6. Hydraulic tubing 32 extend out from the back of either side of flow rate control valve 34, past the artificial knee joint 16, and down along the upper aspect of hydraulic cylinder 24 until tubing 32 enters cylinder 24. The manner of housing control valve 34 and tubing 32 illustrated in FIG. 6 is consistent with the configuration shown for the second preferred embodiment above knee prosthesis 50, and can also be used in other embodiments of the above-knee prosthesis of the present invention wherein control valve 34 is housed within thigh assembly 12 and it is desired that tubing 32 be enclosed together with the other components of the prosthetic device. Enclosing tubing 32 within such other components improves the appearance, convenience and ease of use of the device.

Figure 7:
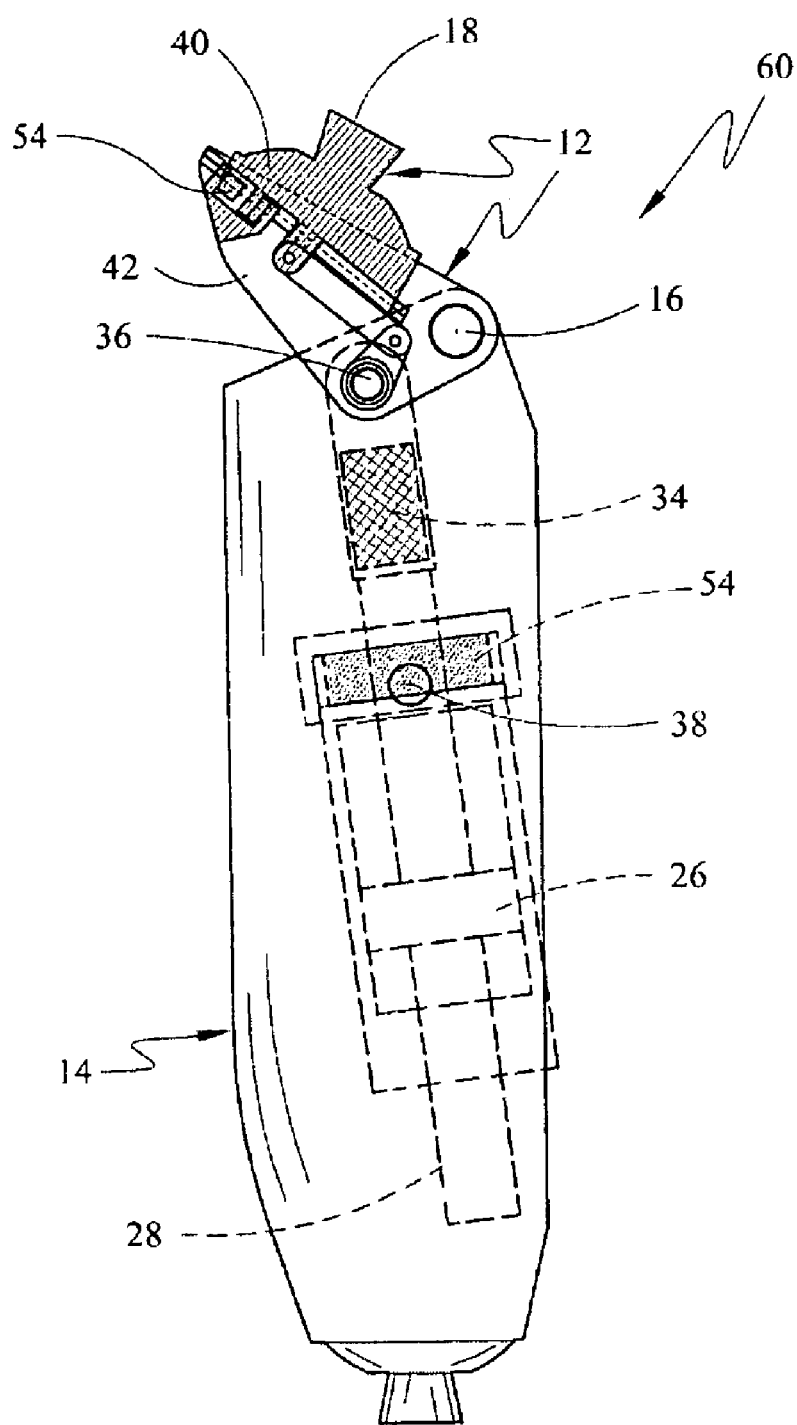
FIG. 7 is a left side view of a third preferred embodiment of the above-knee prosthesis of the present invention wherein the flow rate control valve is housed within the hydraulic system, the right side view being a mirror image thereof.
Figure 8:
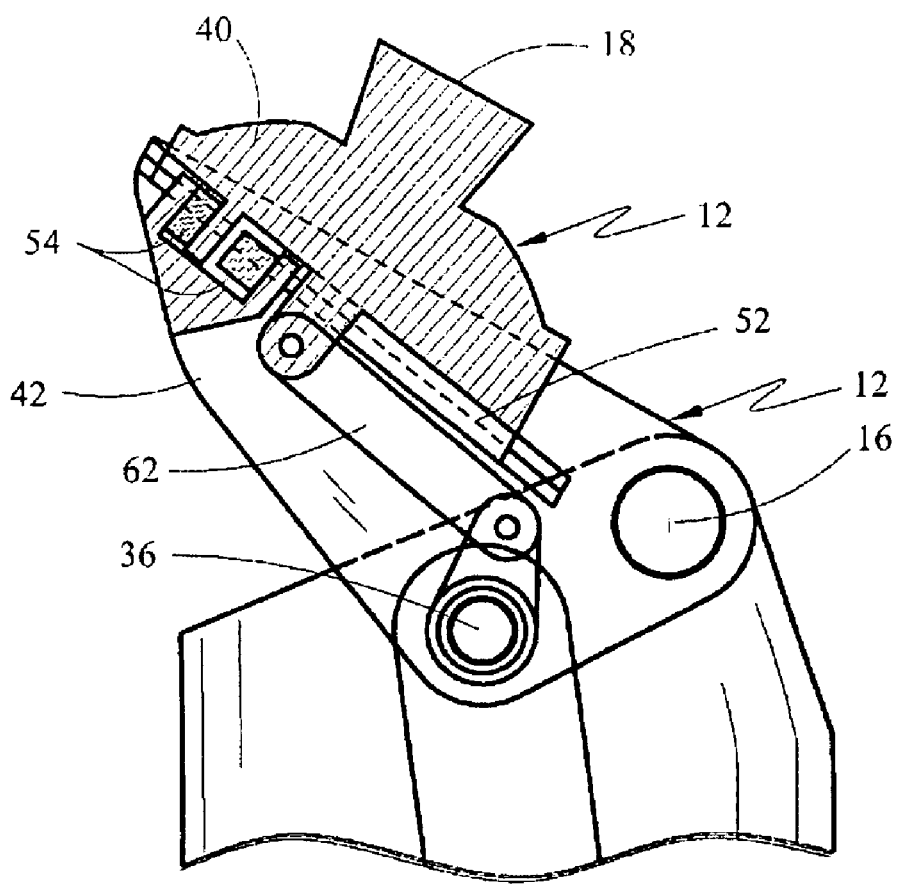
FIG. 8 is a left side view of the above-knee prosthesis of FIG. 7 showing the details and manner of function of the sliding linkage assembly that communicates the AP movement of the thigh stump to the flow rate control valve.
Figure 9:
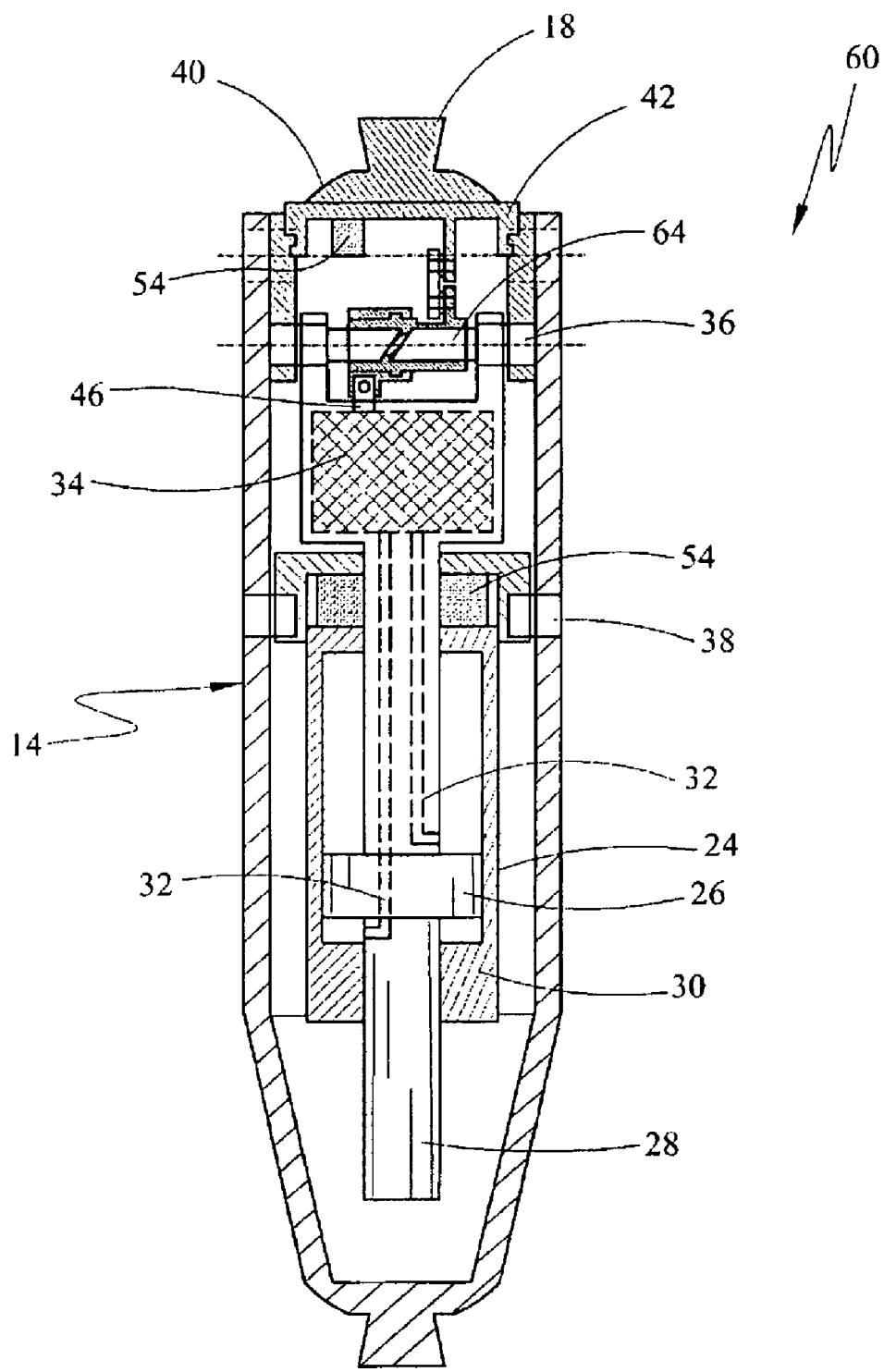
FIG. 9 is a front cross-sectional view of the above-knee prosthesis of FIG. 7 showing the details and manner of function of the sliding linkage assembly that communicates the AP movement of the thigh stump to the flow rate control valve.

Illustrated in FIGS. 7 through 9 is a further preferred embodiment 60 of the above-knee prosthesis of the present invention wherein hydraulic system 22, including flow rate control valve 34, is housed entirely within leg frame assembly 14.

Referring first to FIG. 7, socket 18 appears in this embodiment integrated with upper block 40 of thigh frame assembly 12. When the user causes socket 18 to move upper block 40 relative to lower block 42, a sliding linkage assembly causes flow rate control valve 34 housed within leg assembly 14 to either open or close varying, thereby, the resistance of knee bending.

The details and manner of function of the sliding linkage assembly that serves to communicate the AP movement of the thigh stump to flow rate control valve 34 in preferred embodiment 60 are illustrated in FIGS. 8 and 9. FIG. 8 shows thigh frame assembly 12 of above-knee prosthesis 60, while FIG. 9 shows above-knee prosthesis 60 in cross-section.

Upper block 40 lies facing lower block 42 with slide rail 52 sandwiched between blocks 40 and 42 to facilitate the sliding of blocks 40 and 42 relative to one another. Dampers 54 are placed between lips formed on blocks 40 and 42 to dampen the abutment of these lips at the terminus of each slide.

As block 40 slides along slide rail 52 in an AP direction relative to block 42, a screw linkage 62 communicates this movement to a control screw 64 (shown in FIG. 9) causing control screw 64 to rotate. The rotating movement of control screw 64 is translated into displacement of linkage rod 46 that operates control valve 34. Depending upon the direction of rotation of control screw 64, screw 64 either opens or closes flow rate control valve 34 through linkage rod 46.

Figure 10:
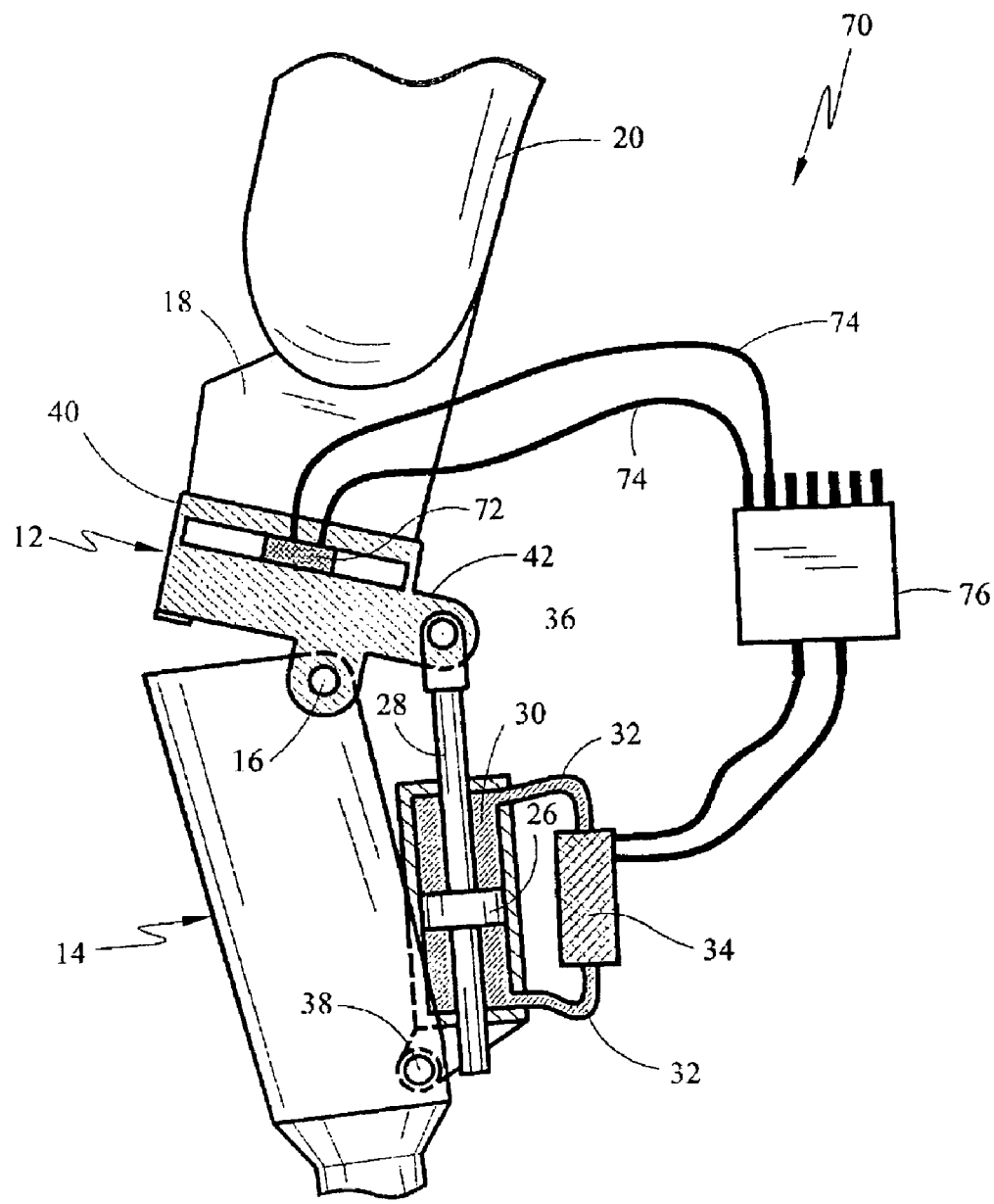
FIG. 10 is a left side view of a fourth preferred embodiment of the above-knee prosthesis of the present invention employing an electronic sensor and microprocessor, the right side view being a mirror image thereof.

FIG. 10 illustrates yet another preferred embodiment 70 of the above-knee prosthesis of the instant invention. Above-knee prosthesis 70 employs a sensor 72 to sense the AP movement of upper block 40 relative to lower block 42. Wires 74 communicate electrical impulses sent by sensor 72 to a micro-processing unit 76. Microprocessor 76, in turn sends signals, based upon the input received from sensor 72, to flow rate control valve 34.

Microprocessor 76 receives input from thigh stump sensor 72, but is configured to also allow it to receive and process input from other sensors (not shown). Such other sensors, known in the art, are attached to the artificial knee and/or ankle to measure ankle movement, knee angle, speed of knee bending, walk cycle, speed of walk cycle, and the like. Information sent by these other sensors are processed together with the data received from thigh stump sensor 72 to provide more sophisticated control of flow rate valve 34 and more intelligent use of the trans-femoral prosthetic device of the subject invention.

SUMMARY AND SCOPE

Accordingly, it will be appreciated that the above-knee prosthesis of the present invention provides the user with a means to control resistance of knee bending regardless of knee angles, through AP movement of the thigh stump. Pressing the thigh stump backwards within the stump socket slows knee bending until the knee locks. Pressing the thigh stump forward allows the artificial knee joint to yield to outside forces, such as gravity and/or stump thrust, until the prosthesis rotates freely about the knee hinge.

Gradual movement of the thigh stump in an AP direction within the prosthetic stump socket enables the wearer to gradually vary the resistance of the artificial knee joint in a continuum from locked, to yielding with strong resistance, to yielding with mild resistance, to rotating freely. With experience, the user of the above-knee prosthesis of the subject invention will develop reflexes such that he or she will unconsciously contract and relax the hip joint extensor and flexor muscles of the thigh stump to increase the resistance of knee bending and, thereby, prevent the giving way of the knee joint.

Because the hydraulically controlled artificial knee joint of the prosthesis of the subject invention can demonstrate variable bend resistance at any given knee angle, the prosthesis facilitates a reciprocating gait close to normal while both while descending as well as ascending slopes and stairs. Also because most of the preferred embodiments of the present invention function mechanically without electronic sensors, and none require a sensor equipped thigh socket, the prosthesis is relatively simple to construct and inexpensive to produce.

While present invention has been described in terms of specific structures reflecting several different preferred embodiments, the invention is not limited to the structures recited in these embodiments. While each of the described embodiments employ a different means of communicating the AP movement of the thigh stump 20 to flow rate control valve 34, other means capable of communicating the AP movement of the thigh stump to the control valve may be employed without departing from the scope and spirit of the subject invention. Similarly, manners of housing hydraulic system 22 within and without thigh assembly 12 and leg assembly 14 are possible beyond those configurations specifically illustrated in conjunction with the above described embodiments. Also, a closed gas cylinder system may be substituted for the closed hydraulic system described, and any number of known improvements for prosthetic leg and foot devices may be employed together with the above-knee prosthesis described herein. Accordingly, the scope of the invention should be determined by the appended claims and their legal equivalents, rather than with reference to any particular example, embodiment or illustration.

What is claimed is:

1. An above-knee prosthesis having a knee joint demonstrating variable resistance comprising a thigh frame assembly that receives a thigh stump, a leg frame assembly with foot attached, a hinge interconnecting said thigh frame and leg frame assemblies to form an artificial knee joint, a closed hydraulic system further interconnecting said thigh frame and leg frame assemblies above and below said hinge to provide resistance to the flexion or extension of said artificial knee joint, a means to vary the resistance provided by said closed hydraulic system, and a means to translate the anterior-posterior ("AP") movement of said thigh stump into the degree of resistance provided by said closed hydraulic system that functions independent of knee angle.

2. The above-knee prosthesis of claim 1, wherein the means to vary the resistance provided by said closed hydraulic system comprises a flow rate control valve.

3. The above-knee prosthesis of claim 2, wherein the means of translating the AP movement of said thigh stump to the degree of resistance provided by said closed hydraulic comprises a mechanical linkage mechanism that communicates the AP movement of said thigh stump to said flow rate control valve.

4. The above-knee prosthesis of claim 2, wherein the means of translating the AP movement of said thigh stump to the degree of resistance provided by said closed hydraulic comprises a sliding mechanism that communicates the AP movement of said thigh stump to said flow rate control valve.

5. The above-knee prosthesis of claim 2, wherein the means of translating the AP movement of said thigh stump to the degree of resistance provided by said closed hydraulic comprises an electronic sensor and microprocessor wherein said sensor communicates movement of said thigh stump by electronic impulse to said microprocessor and said microprocessor further communicates said thigh movement by electronic impulse to said flow rate control valve.

6. The above-knee prosthesis of claim 5, further comprising additional sensors attached to the knee and ankle that provide information to said microprocessor that is combined with the information provided by the thigh stump sensor to more intelligently control said flow rate control valve.

7. The above-knee prosthesis of claim 1 wherein said closed hydraulic system is housed substantially within said thigh and leg frame assemblies.

8. The above-knee prosthesis of claim 1 wherein said closed hydraulic system is housed substantially outside said thigh and leg frame assemblies.

9. The above-knee prosthesis of claim 2 wherein said flow rate control valve is housed within said thigh frame assembly.

10. The above-knee prosthesis of claim 2 wherein said flow rate control valve is housed within said leg frame assembly and said mechanical linkage mechanism if configured to communicate the AP movement of the thigh stump to said flow rate control valve independent of knee angle.

11. A method of improved mobility for above-knee prostheses comprising the steps of:

providing a thigh frame assembly that receives a thigh stump;

providing a leg frame assembly with foot attached; interconnecting said thigh frame and leg frame assemblies with a hinge to form an artificial knee joint;

providing a closed hydraulic system that further interconnects said thigh frame and leg frame assemblies above and below said hinge to provide resistance to the flexion or extension of said artificial knee joint;

providing a means to vary the resistance provided by said closed hydraulic system together with a means to translate the anterior-posterior ("AP") movement of said thigh stump into the degree of resistance provided by said closed hydraulic system that functions independent of knee angle, such that moving the thigh stump in an anterior direction decreases the resistance of rotation within said artificial knee joint and moving the thigh stump in a posterior direction increases the resistance of rotation within said artificial knee joint.

12. The method of claim 11, wherein the means to vary the resistance provided by said closed hydraulic system comprises a flow rate control valve.

13. The method of claim 11, wherein the means of translating the AP movement of said thigh stump into the degree of resistance provided by said closed hydraulic system comprises a mechanical linkage mechanism that communicates the AP movement of said thigh stump to said flow rate control valve.

14. The method of claim 11, wherein the means of translating the AP movement of said thigh stump into the degree of resistance provided by said closed hydraulic system comprises a sliding mechanism that communicates the AP movement of said thigh stump to said flow rate control valve.

15. The method of claim 11, wherein the means of translating the AP movement of said thigh stump into the degree of resistance provided by said closed hydraulic system comprises an electronic sensor and microprocessor wherein said sensor communicates movement of said thigh stump by electronic impulse to said microprocessor and said microprocessor further communicates said thigh movement by electronic impulse to said flow rate control valve.

16. The method of claim 15, further comprising additional sensors attached to the knee and ankle that provide information to said microprocessor that is combined with the information provided by the thigh stump sensor to more intelligently control said flow rate control valve.

17. The method of claim 11, wherein said closed hydraulic system is housed substantially within said thigh and leg frame assemblies.

18. The method of claim 11, wherein said closed hydraulic system is housed substantially outside said thigh and leg frame assemblies.

19. The method of claim 11, wherein said flow rate control valve is housed within said thigh frame assembly.

20. The method of claim 11, wherein said flow rate control valve is housed within said leg frame assembly and said mechanical linkage mechanism if configured to communicate the AP movement of the thigh stump to said flow rate control valve independent of knee angle.

* * * * *